United States Patent
Hakuk et al.

(10) Patent No.: US 10,572,997 B2
(45) Date of Patent: Feb. 25, 2020

(54) SYSTEM AND METHOD FOR DETECTING ANOMALIES IN AN IMAGE CAPTURED IN-VIVO USING COLOR HISTOGRAM ASSOCIATION

(71) Applicant: GIVEN IMAGING LTD., Yoqneam (IL)

(72) Inventors: Yaron Hakuk, Giv'at Shmuel (IL); Dori Peleg, Haifa (IL)

(73) Assignee: GIVEN IMAGING LTD., Yoqneam (IL)

( * ) Notice: Subject to any disclaimer, the term of this patent is extended or adjusted under 35 U.S.C. 154(b) by 152 days.

(21) Appl. No.: 15/381,604

(22) Filed: Dec. 16, 2016

(65) Prior Publication Data

US 2017/0178322 A1    Jun. 22, 2017

Related U.S. Application Data

(60) Provisional application No. 62/269,505, filed on Dec. 18, 2015.

(51) Int. Cl.
*G06K 9/52* (2006.01)
*A61B 1/00* (2006.01)
(Continued)

(52) U.S. Cl.
CPC ........ *G06T 7/0012* (2013.01); *A61B 1/00009* (2013.01); *A61B 1/041* (2013.01); *G06K 9/4642* (2013.01); *G06K 9/4652* (2013.01); *G06K 9/52* (2013.01); *G06K 9/6267* (2013.01); *G06T 2207/30004* (2013.01)

(58) Field of Classification Search
None
See application file for complete search history.

(56) References Cited

U.S. PATENT DOCUMENTS 3,683,389 A    8/1972   Hollis
3,888,237 A    6/1975   Mori
(Continued)

OTHER PUBLICATIONS

Adam Blokus, Adam Brzeski, Jan Cychners, "Real-Time Bleeding Detection in Gastrointestinal Tract Endoscopic Examinations Video," Department of Computer Architecture, Gdańsk Technical University, Poland (Jul. 2013).

*Primary Examiner* — Tahmina N Ansari
(74) *Attorney, Agent, or Firm* — Pearl Cohen Zedek Latzer Baratz LLP

(57) ABSTRACT

Systems and methods for detecting an anomaly in an image from a set of images captured in vivo by an in-vivo imaging system may include, for each pixel of the image, associating the pixel with a color histogram value from a color histogram database; determining, for each pixel, whether the color histogram value associated with the pixel exceeds a histogram value threshold; assigning a pixel status to each pixel indicating whether the pixel is anomalous or normal; identifying one or more groups of adjacent anomalous pixels, the one or more groups of adjacent anomalous pixels each having a pixel size that exceeds a pixel size threshold; generating, using at least the one or more groups of adjacent anomalous pixels, a binary mask for the image; and determining an image anomaly score for the image based at least in part on the binary mask.

25 Claims, 8 Drawing Sheets
(4 of 8 Drawing Sheet(s) Filed in Color)

(51) Int. Cl.
  *G06T 7/00* (2017.01)
  *G06K 9/46* (2006.01)
  *G06K 9/62* (2006.01)
  *A61B 1/04* (2006.01)

(56) References Cited

U.S. PATENT DOCUMENTS

| | | |
|---|---|---|
| 3,971,362 A | 7/1976 | Pope et al. |
| 4,278,077 A | 7/1981 | Mizumoto |
| 4,689,621 A | 8/1987 | Kleinberg |
| 4,741,327 A | 5/1988 | Yabe |
| 5,604,531 A | 2/1997 | Iddan et al. |
| 7,009,634 B2 | 3/2006 | Iddan et al. |
| 8,189,890 B2 | 5/2012 | Summers et al. |
| 8,819,890 B2 | 9/2014 | Lin |
| 8,861,783 B1 | 10/2014 | Peleg |
| 8,873,816 B1 | 10/2014 | Peleg et al. |
| 8,913,807 B1 | 12/2014 | Horn et al. |
| 9,082,165 B2 | 7/2015 | Guissin |
| 9,342,881 B1 | 5/2016 | Peleg |
| 2002/0177779 A1 | 11/2002 | Adler et al. |
| 2008/0119740 A1 | 5/2008 | Iddan |
| 2012/0316421 A1 | 12/2012 | Kumar et al. |
| 2013/0109915 A1* | 5/2013 | Krupnik ............ G06T 3/4038 600/109 |

\* cited by examiner

SYSTEM AND METHOD FOR DETECTING ANOMALIES IN AN IMAGE CAPTURED IN-VIVO USING COLOR HISTOGRAM ASSOCIATION

PRIOR APPLICATION DATA

The present application claims benefit from prior U.S. provisional application 62/269,505, filed on Dec. 18, 2015, entitled "SYSTEM AND METHOD FOR DETECTING ANOMALIES IN AN IMAGE CAPTURED IN-VIVO", incorporated herein by reference in its entirety.

FIELD OF THE INVENTION

The present invention relates to the field of anomaly detection. More specifically, the present invention relates to automatically detecting anomalies in a tissue. In particular, embodiments of the present invention relate to detecting anomalies in an image of a tissue captured by an in-vivo device.

BACKGROUND OF THE INVENTION

Known devices may be helpful in providing in-vivo sensing, for example, using imaging techniques, systems and/or methods. One of the uses of such devices may involve visual detection and/or identification of objects or tissues that may be or include in-vivo anomalies (e.g., pathologies). Autonomous in-vivo sensing devices, e.g., swallowable or ingestible capsules, may move through a body lumen, and sense, monitor or otherwise obtain data as they move along/through the gastrointestinal ("GI") system or other body lumens. An autonomous in-vivo sensing device may include, for example, an imager for obtaining images of a body cavity or lumen, such as the GI tract. An autonomous in-vivo sensing device may also include an optical system, a light source, a controller and optionally a transmitter and an antenna. Some of these devices transfer image data wirelessly.

Although high quality data may be produced and provided by in-vivo sensing devices, e.g., high resolution images or video streams, analyzing the data may be costly and/or time consuming. For example, identifying an anomaly in a video stream produced by an in-vivo device traveling through the GI tract may require hours since the entire video may have to be examined, possibly by a physician or trained person or healthcare professional. It would be, therefore, beneficial to detect anomalies in imaged tissues automatically.

U.S. Pat. No. 8,913,807 (hereinafter, "the '807 patent, which is incorporated herein by reference in its entirety) describes a system and method for detecting anomalies in a color image of a tissue of the GI system by segmenting the color image into valid tissue zones and non-valid tissue zones. According to the '807 patent, a valid tissue zone may be a zone within an image whose pixels have intensities that are higher than a predetermined intensity reference and are relatively uniform, e.g., their intensities or gray levels do not change significantly across the zone. For example, these pixels may have a relatively small variance in terms of intensity or gray level. Then, one or more anomaly regions may be searched for in each valid tissue zone based on a comparison between color parameters of the pixels making up the valid tissue zone and reference color characteristics. A pixel within a valid tissue zone may be categorized, or marked, as an "anomalous pixel" or as a "normal" (e.g., regular, or healthy) pixel based on the comparison result, and a region may be regarded as an "anomaly region" if the region's pixels or a group of pixels satisfy a predetermined anomaly criteria or property, such as density of anomalous pixels, percentage of anomalous pixels, or other criteria.

Systems and methods are needed which are not limited to only detecting red pathologies, or requiring image areas whose boundaries can be detected by using high color gradients. Furthermore, systems and methods are needed, which may update thresholds associated with the systems and methods using images in new image streams. Such new systems and methods are needed to avoid the triggering of many false alarms, for example. As such, new solutions are needed which resolve these and other limitations in existing systems and methods.

SUMMARY OF EMBODIMENTS OF THE INVENTION

According to embodiments of the invention, there are provided systems and methods for detecting an anomaly in an image from a set of images captured in vivo by an in-vivo imaging system. Embodiments of the invention may be performed on a computer, for example, having a processor, a memory, and one or more code sets stored in the memory and executed in or by the processor. In some embodiments, for each pixel of the image, the processor may associate the pixel with a color histogram value from a color histogram database; determine, for each pixel, whether or not the color histogram value associated with the pixel exceeds a histogram value threshold; in which an associated color histogram value that does not exceed the histogram value threshold indicates an anomalous pixel, and in which an associated color histogram value that exceeds the histogram value threshold indicates a normal pixel; assign a pixel status to each pixel, the pixel status indicating whether or not the pixel is anomalous or normal; identify one or more groups of adjacent anomalous pixels, each of the one or more groups of adjacent anomalous pixels having a pixel size that exceeds a pixel size threshold; generate, using at least the one or more groups of adjacent anomalous pixels, a binary mask for the image, the binary mask including an aggregated pixel size which, in some embodiments, may be a pixel size of, or representing, the one or more identified groups (of adjacent anomalous pixels) that exceed the pixel size threshold; and determine or derive (e.g., calculate) an image anomaly score for the image, based at least in part on or using the binary mask.

In some embodiments, the color histogram database may be, e.g., a representation of a prevalence of {R,G,B} color values in a set of previously analyzed images. In some embodiments, a given color histogram value may represent a prevalence of a particular combination of {R,G,B} color values in a set of previously analyzed images; and a given color histogram value may be associated with a given pixel, (e.g., a particular color histogram value may be associated with a particular pixel), for example, based on the particular combination of {R,G,B} color values which make up the given pixel color (e.g., the particular pixel color) in the image. In some embodiments, the pixel status of each pixel may be indicated as a binary numeral or value. In some embodiments, the step of indicating the pixel status of each pixel may include generating a binary matrix of the image, in which the pixel status of each pixel may be represented by an 'anomalous' value (e.g., the value '1') when the pixel is anomalous, and by a 'normal' value (e.g., the value '0') when the pixel is normal. In some embodiments, the image anomaly score may be determined based on a pixel size of the binary mask of the image and a mean histogram value of the pixels in, or making, the binary mask.

In some embodiments, a processor may generate a final anomaly score image, e.g., based on the correlated histogram value of each pixel in the image, and the binary mask. In some embodiments, for a set of generated anomaly score images, the processor may select a subset of the anomaly score images with or having the highest, or relatively high, image anomaly scores, and add the selected subset of anomaly score images to the set of images. In some embodiments, the aggregated pixel size may include or represent an aggregation of pixel sizes calculated for the one or more identified groups.

In accordance with further embodiments, systems may be provided, which may be configured to perform embodiments of the methods described herein. These and other aspects, features and advantages will be understood with reference to the following description of certain embodiments of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee. Embodiments of the invention are illustrated by way of example and not limitation in the figures of the accompanying drawings, in which like reference numerals indicate corresponding, analogous or similar elements, and in which.

Figure 1A:
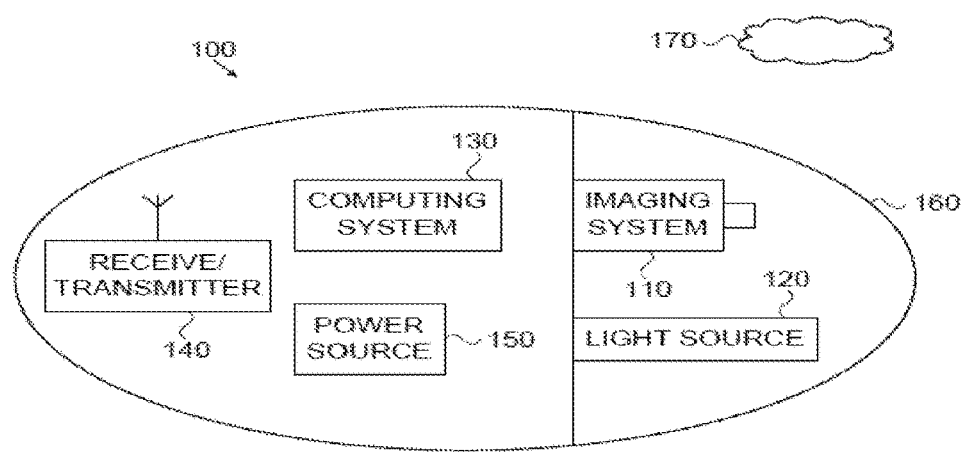
FIG. 1A is a block diagram of an in-vivo imaging system according to an example embodiment of the invention.

It will be appreciated that for simplicity and clarity of illustration, elements shown in the figures have not necessarily been drawn accurately or to scale. For example, dimensions of some of the elements may be exaggerated or more emphasized relative to other elements for clarity, or several physical components may be included in one functional block or element. Further, where considered appropriate, reference numerals may be repeated among the figures to indicate corresponding or analogous elements.

DETAILED DESCRIPTION OF EMBODIMENTS OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently.

Embodiments of the systems and methods of the present invention may be used in conjunction with an imaging system or device capable of obtaining images of in-vivo objects. More specifically, in some embodiments, any imaging device or system that may be incorporated into an in-vivo device may be used. However, it will be understood that embodiments of the invention are not limited by the type, nature or other aspects of the imaging system, device or unit used.

An in-vivo imaging device may capture a series of images as it traverses the GI system, and transmit the images, typically by transmitting one image frame at a time. The images may be later compiled at a receiver to produce a displayable video clip or an image stream, or a series of images. An image transmitted by the in-vivo imaging device to the receiver may be a color image. In one example, each image may include 256 rows of 256 pixels each, where each pixel may be represented, or has associated therewith, binary data (e.g., bytes) that may represent, for example, the pixel's color and brightness. For example, color may be produced from, or by using, a mosaic of four pixels, where each pixel may represent, or correspond to, a primary color such as red, green, or blue. (A primary color, e.g., green, may be represented twice; e.g., by two pixels of the mosaic). Image data may be stored sequentially in a storage unit. The image data may include one or more pixel properties, including color, intensity and brightness. Any pixel's parameter, e.g., intensity, color, hue, brightness, luminance, chromaticity and/or saturation of one or more colors may likewise be encoded and attributed to, or associated with any pixel in an image captured by an in-vivo or other device.

Detection of an anomaly in a tissue imaged by an imaging device may include measuring one or more pixel parameters (e.g., color parameter) of one or more pixels in an image. An anomaly detected as described herein may be any pathology, e.g., a polyp, a lesion, a tumor, an ulcer, a blood spot, an angiodysplasia, a cyst, a choristoma, a hamartoma, a tissue malformation, a nodule, to list some example pathologies, or any irregularity which may not be identified as a healthy tissue.

FIG. 1A shows a schematic diagram of an in-vivo imaging device 100 according to an example embodiment. In-vivo imaging device 100 may include an imaging system 110, a light source 120, a computing system 130, a receiver/transmitter 140, a power source 150 (e.g., an internal battery or a wireless energy picking system) and a viewing window or dome 160. In some embodiments, in-vivo imaging device 100 may be, for example, a swallowable capsule capable of capturing images and/or obtain other data. More specifically, in-vivo device 100 may independently obtain images, process images, store images and other information, communicate images to a remote computing or communication device and/or provide information, data or parameters related to obtained and/or processed images. For example, while inside a body of a human or other mammal, in-vivo device 100 may obtain images of tissues, objects or their surroundings, and/or the surroundings of in-vivo device 100, and store, process and/or communicate the obtained images as well as calculate, compute, determine and provide various indications, alarms, values, results, measurement values, or measurement results (herein generally referred to as "results"). In some embodiments, the configuration of components may be similar to, for example, that of U.S. Pat. No. 7,009,634, incorporated by reference herein. Other configurations may be used.

In-vivo device 100 may have a shape of a capsule, as demonstrated in FIG. 1A, including for example a viewing window or dome 160. Viewing window 160 may be convex or substantially convex and smooth, and may project outward from the main body and/or housing of device 110. Viewing window 160 may be designed to provide a suitable field of view ("FOV") for imaging system 110 and/or to enable light from light source 120 to reach objects or tissues outside device 110, e.g., tissue 170 as shown. Other shapes may be used, and the device need not be swallowable or a capsule. For example, device 100 may be implanted, inserted or otherwise located in any applicable location.

Imaging system 110 may be any suitable imaging system. For example, imaging system 110 may include any number of lenses or mirrors, or support assemblies that may be used to direct imaging system 110 at a specific direction or angle and/or an embedded control module. Imaging system 110 may include a complementary metal oxide semiconductor (CMOS) imaging camera. As known in the art, a CMOS imager is typically an ultra-low power imager and is provided in chip scale packaging (CSP). Other types of CMOS or other imagers may be used, e.g., a CCD imager. A 320×320 pixel imager, for example, may be included in imaging system 110, e.g., each pixel being between 5 to 6 microns. According to some embodiments pixels may be each fitted with a micro lens.

Light source 120 may be any suitable light or energy source capable of producing, e.g., periodically or continually, light or other form of energy that may interact with tissues or objects outside device 100, e.g., tissue 170 shown in FIG. 1A. For example, light emitted periodically or continually by light source 120 may be reflected from the objects and captured by imaging system 110. For example, light source 120 may be a set of light emitting diodes (LEDs), organic LEDs (OLEDs), or other suitable light sources, may provide light to illuminate objects thus enable acquiring images as known in the art. In other embodiments, other forms of energy or types of light may be produced by light source 120, e.g., any form light or energy that imaging system 110 is capable of acquiring.

Computing system 130 may be any suitable article, processor, chip, controller or suitable computing device suitable for processing images as described herein as well as controlling components in device 100. For example, computing system 130 may perform one or more of the following: causing imaging system 110 to acquire an image, process the image, cause the image to be stored on a local storage (not shown) in device 100, cause the image to be communicated to a remote device, e.g., by controlling transmitter/receiver 140 and the like. In some embodiments, computing system 130 need not be a separate component; for example, parts of computing system 130 may be integral to, or embedded in, imaging system 110 or receiver transmitter 140. The functionality of computing system 130 may be performed by other components of device 100.

Transmitter/receiver 140 may transmit and/or receive images and/or other (e.g., non-image) information to/from a remote device. For example, a computer configured to wirelessly communicate with device 100 may be placed near a patient and may wirelessly communicate with device 100. Transmitter/receiver 140 may be an ultra-low power radio frequency (RF) transmitter with high bandwidth input, possibly provided in chip scale packaging, may be combined with a processing chip or circuit and may transmit and/or receive information via an antenna as shown. Device 100 may include a power source 150, such as one or more batteries. For example, power source 150 may include silver oxide batteries, lithium batteries, or other electrochemical cells having a high energy density, or the like. Other power sources may be used. Other components, modules or units may be used. For example, power source 150 may be capable of receiving power from an external power source transmitting power to the device 100.

Embodiments of device 100 may typically be autonomous and/or self-contained. For example, the device may be a capsule or other unit where components are substantially contained within a container or shell, and where the device does not require any wires or cables to, for example, receive power, obtain, store or transmit information etc. Device 100 may communicate with an external computing or communication system that may receive, process, store, communicate and display images or other data or information received from device 100. The remote system or device may further be used to control device 100. Accordingly, it will be understood that processing of digital images and detecting anomalies in a tissue captured in images as described herein may be performed by a remote computing system configured to receive images acquired by in-vivo device 100.

In some embodiments, some or all of the processing of images as described herein may be performed by device 100, e.g., using computing system 130. In other embodiments, device 100 may perform some of the processing described herein and another computing system, e.g., a remote system may perform other processing or tasks. In yet other embodiments, device 100 may only obtain images, perform limited or no processing of the acquired images and send the images to a remote computing device or system which may perform processing, analyzing and determining of various parameters based on received images. For example, a, remote system may display images to a physician, receive a selection from the physician and detect an anomaly in a tissue shown in an image based on the physician's selection.

Figure 1B:
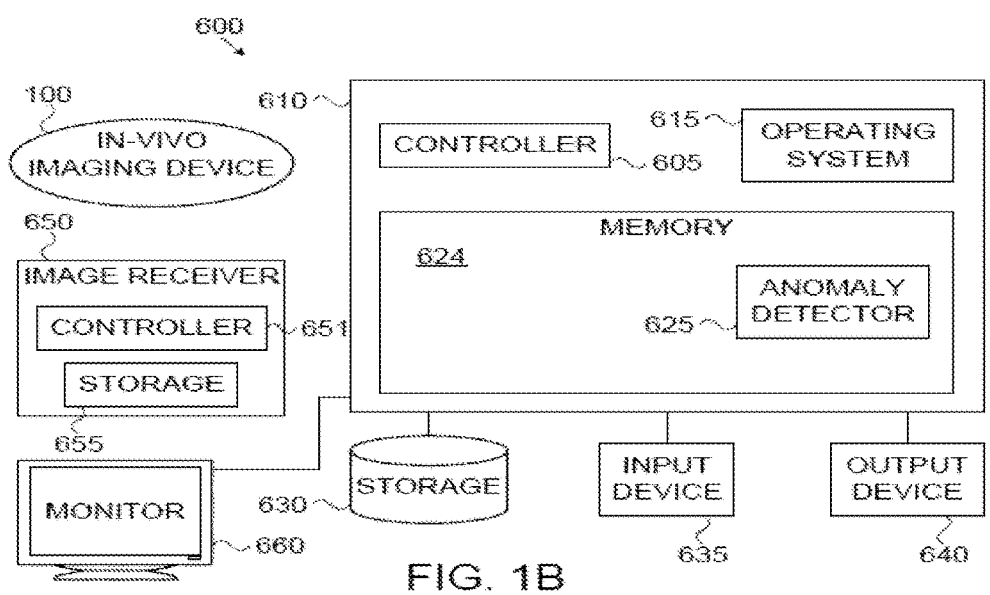
FIG. 1B is a block diagram of an in-vivo imaging system according to an example embodiment of the invention.

FIG. 1B shows an example block diagram of an in-vivo imaging system 600, according to an example embodiment. System 600 may include an in-vivo imaging device, for example, in-vivo imaging device 100. In-vivo imaging device 100 may communicate with a receiving and display system external to the patient to provide display of data, control, or other functions. System 600 may include a receiver 650 including processor or controller 651, for example to receive images from in-vivo imaging device 100, and a storage 655. For brevity, various components that may be installed or included in image receiver 650 are not shown. For example, image receiver 650 may include output and input ("I/O") components, interface, or devices, which may be similar to input device 635, and an output device 640 and/or an operating system similar to operating system 615, memory similar to memory 624, etc. Image receiver 650 may be any suitable computing device that may perform any function, process or operation including for example those related to the detection of anomalies or pathologies in images, as described herein.

Image receiver 650, which may include an antenna or antenna array, an image receiver storage unit 655 and a data processor or controller, may in some embodiments be a small device that can be worn and carried by a patient. For example, an (e.g. ambulatory) patient may wear image receiver 650 on a belt or wrist. Image receiver 650 may communicate, e.g., wirelessly, with in-vivo device 100, receive, from in-vivo device 100, images and store received images on storage 655. Image receiver 650 may collect images captured by in-vivo imaging device 100 over a relatively long period of time. Image receiver 650 may be configured to communicate, wirelessly or otherwise, with computing system 610 and transfer images and/or other information to computing system 610. For example, images and/or other information received from in-vivo imaging device 100 may be stored on storage 655 and may be transferred from storage 655 to computing system 610, e.g., using wireless communication, a universal serial bus (USB) connection or another communication method.

Computing system 610 may analyze and/or process images captured by in-vivo device 100 to detect anomalies (among other things). Computing system 610 may receive images directly from in-vivo device 100 or via image receiver 650, and may detect anomalies in tissues imaged by in-vivo device 100. Various operations and tasks that may be performed by computing system 610 may be performed by in-vivo imaging device 100, e.g., by computing system 130 or, in other embodiments, by image receiver 650.

System 610, which may be for example a workstation or other computer, may store an image or a series of images captured by in-vivo imaging device 100 in memory 624, and processor/controller 605 may be configured to perform functions described herein, such as to select image pixels associated with the imaged object, analyze pixel color parameters of the selected pixels, and perform various calculations related to the pixels and/or associated parameters. For example, controller 605 may mark a pixel as an "anomalous pixel" based on pixel color values of the pixel. Controller 605, by executing software or code may, for example, correlate or associate, for each pixel of an image, a histogram value from a histogram database with, or corresponding to, the pixel; determine, for each pixel, whether or not the correlated, or associated, histogram value exceeds a histogram value threshold (e.g., whether the pixel has such a value); assign, for each pixel, or for selected pixels, a pixel status or value (the pixel status indicating, e.g., whether the pixel is anomalous or normal); identify one or more groups of adjacent anomalous pixels; generate, calculate, create and/or otherwise produce a binary mask for the image using at least the one or more groups of adjacent anomalous pixels; and determine an image anomaly score for the image based on the image and/or the binary mask of the image. Of course, other processes and calculations may also be performed, as described herein.

Selection of pixels for evaluation and performing tasks, processes and functions described herein may be performed by controller 651, or by controller 605, or by both controllers 651 and 605. Each of controller 651 and controller 605 may be a computer processor configured to carry out methods described herein by, for example, executing software instructions or code. In some embodiments, detection of an anomaly in an imaged object or imaged tissue may be distributed among controllers, processors or computing systems. For example, computing system 130 and controllers 605 and 651 may share computational tasks or calculations in order to detect an anomaly, tissue, organ, and/or extraneous visual artifacts in an image. Computing system 130 and controllers 605 and 651 may communicate or exchange (e.g., over wireless or wired links) any data, parameters or information. Computing system 130 and controllers 605 and 651 may share computational resources in performing the tasks or methods described herein.

In some embodiments, processing of images performed in order to detect anomalies or pathologies may be distributed. For example, an image may be modified or adjusted, for example, by in-vivo device 100, or by computing system 130. For example, light parameters/values (light intensity, color, hue, etc.) of, or associated with, pixels may be altered, modified or adjusted based on parameters which may be device specific, e.g., specific to a lens, specific to a light source, etc. The pre-processed image may, then, be communicated to system 610 which may detect anomalies or pathologies in images of tissues.

Controller 605 may be, for example, a central processing unit processor (CPU), a chip or any suitable computing or computational device, an operating system 615, a memory 624, a storage 630, an input device 635 and an output device 640. Operating system 615 may be or may include any code segment designed and/or configured to perform tasks involving coordination, scheduling, arbitration, supervising, controlling or otherwise managing the operation of computing system 610, for example, scheduling execution of programs loaded into memory 624.

Anomaly detector 625 may be a dedicated processor and/or any executable code, e.g., an application, a program, a process, task or script. Anomaly detector 625 may be executed by controller 605 possibly under control of operating system 615. Thus anomaly detector 625 and other modules described herein may be controller 605 or another controller or processor described herein. For example, anomaly detector 625 may be an application designed to analyze an image and detect anomalies or pathologies in an imaged object (e.g., a GI tissue). Storage 630 may be or may include, for example, a hard disk drive, a floppy disk drive, a Compact Disk (CD) drive, a CD-Recordable (CD-R) drive, a universal serial bus (USB) device or other suitable removable and/or fixed storage unit. Input device 635 may be or may include a mouse, a point-and-click device, a keyboard, a touch screen or pad or any suitable input device. In some embodiments, input device 635 may be an input port. For example, an input port (e.g., a network interface card (NIC), a USB port or a wireless port or card) may be used to receive images from image recorder 650, in-vivo device 100, or an external storage. It will be recognized that any suitable number of input devices may be operatively connected to computing system 610. Output device 640 may include one or more displays, speakers and/or any other suitable output device. It will be recognized that any suitable number of output devices may be operatively connected to computing system 610. Any suitable input/output (I/O) device may be connected to, and used to interact with, computing system 610.

Images obtained by in-vivo device 100 and provided to computing system 610 may be displayed on monitor 660. Any result or indication may be displayed on monitor 660. For example, an anomaly may be displayed on monitor 660 by displaying the image containing the anomaly, and superimposing a visual indication on the anomaly. Input device 635 (e.g., a mouse or keyboard) may be used by a user to indicate objects, tissues or regions of interest in an image, and an anomaly may be searched for and/or detected in an indicated area or portion of that image. A tissue or a tissue portion or region where an anomaly may be searched for and/or detected may be selected based on an indication of interest received from a user. For example, a user may click or otherwise indicate (e.g., using a pointing device such as a mouse, a stylus, etc.) a location in an image, circle a location or otherwise indicate a tissue, organ or region of interest, and an anomaly in the selected or indicated area, tissue or organ imaged by the in-vivo device may be performed as described herein. Some functions or tasks that are performed by anomaly detector 625 may be implemented in hardware (e.g., by using an application-specific integrated circuit ("ASIC") or chip), or they may be implemented in firmware.

A physician may use system 600 to indicate or mark an object of interest and/or indicate or mark a particular area in an image (e.g., in a displayed image) for anomaly analysis. For example, the physician may observe an image of tissue 170 (tissue 170 is shown in FIG. 1A) and use, for example, input device 635 to point to or mark a region or area of interest (e.g., a region or area suspected as being anomaly), and the marked region or area, or the region/area pointed to, may be analyzed, and an anomaly may be automatically detected in the indicated/marked region/area. An area suspected as having an anomaly may be selected automatically, e.g., based on various attributes (e.g., color parameters) such as color, hue, saturation, or reflected light intensity that may significantly differ from attributes of the surrounding environment, e.g., adjacent or nearby tissue or cavities. Detection of anomalies in the colon and small bowel may be of particular interest, but it may likewise be applicable to other organs or tissues.

An anomaly in a tissue may exhibit, or be associated with, traits such as a specific color or other specific values that may be detected by examining pixel color parameters of pixels in an image. For example, anomalies such as a polyp, a lesion, a tumor, a blood spot, an angiodysplasia, a cyst, a choristoma, a hamartoma, a tissue malformation or a nodule may be characterized by having pixel parameter(s) (e.g., color, saturation, intensity or other color parameters) that may differ from pixel parameters associated with, or be conspicuous relative to, a normal or healthy tissue.

Figure 4:
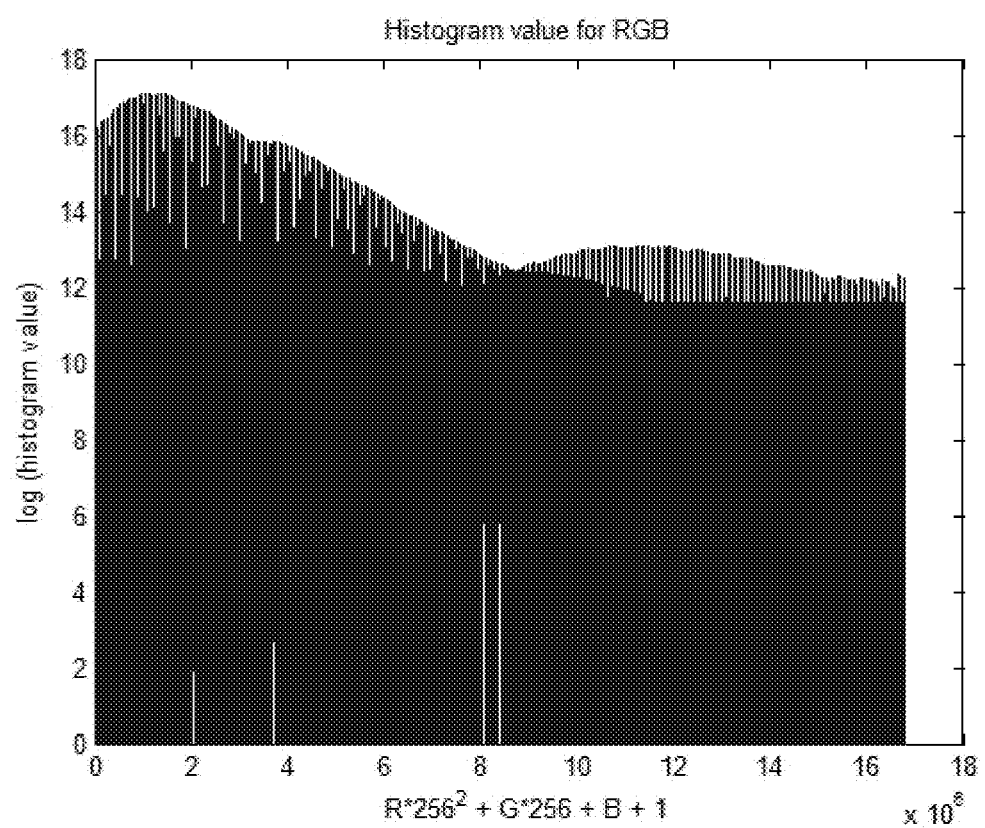
FIG. 4 shows an example color histogram according to an example embodiment of the invention.

As such, turning to FIG. 4, in accordance with various embodiments of the invention, a color histogram may be generated and/or used to determine whether or not an image is, or includes, an anomaly, for example, based on color values in the image. A color histogram, as used herein, is a representation of a distribution (e.g., a statistical distribution), or prevalence (e.g., a statistical prevalence), of colors that appear in images. In particular, a color histogram is a statistical representation (with respect to the prevalence of colors) that can be viewed as an approximation of an underlying continuous distribution of color values amongst one or more images. For example, while some colors are statistically more likely to be found in images of healthy tissues, other colors are statistically more likely to be found in images of unhealthy tissues. A color histogram may show numbers of pixels that respectively have certain colors in various color ranges, in which the color ranges may span an image's color space (e.g., the set of all possible colors which may appear in images taken inside the GI system).

In various embodiments, a color histogram may be calculated, generated, built, or created for different types of color spaces, such as, for example, three-dimensional spaces (e.g., the Red-Green-Blue ("{R,G,B}") color space). In some embodiments, the combination of {R,G,B} values of each pixel (or of selected pixels) may be counted or tallied, for example, as a "1" (e.g., "1" representing the presence of a particular combination of {R,G,B} values; e.g., color, in that pixel), and added to the histogram data in the appropriate place. That is, if a particular {R,G,B} combination (or a similar combination), hence a corresponding histogram value, associated with a particular pixel is also associated with other pixels, the histogram data may be updated with the number of times the particular histogram value resulted from such calculations. As such, each time a particular combination of {R,G,B} values is detected anywhere in the image (e.g., in multiple pixels), the tally count in the histogram data is increased by one. In some embodiments, e.g., where smoothing the histogram is required or desired, every {R,G,B} value whose color-wise 'distance' from another pixel's {R,G,B} value is relatively short (e.g., less than a predetermined threshold value; e.g., less than 3 'values'), for example, may also be counted as a "1" and added to the histogram data.

For multi-spectral images, where each pixel is represented by an arbitrary number of measurements (for example, beyond the three measurements in {R,G,B}), the color histogram may be N-dimensional, with N being the number of measurements taken. Each measurement may have its own wavelength range of the light spectrum, some of which may be outside the visible spectrum, for example.

In some embodiments, the color histogram may be represented by a vector (or vectors) that includes, or is made of, or has a vector length of, e.g., $256^3$ 'places', 'locations' or 'positions'; e.g., 1, 2, 3, ... 16,777,216 ($=256^3$). A particular location (L) of a pixel's color on the histogram vector may be determined, e.g., based on the combination of its {R,G,B} values, for example by using the following formula:

$$L = R(256^2) + G(256) + B + 1$$

$$(L_{Max.} = 255 \times 256^2 + 255 \times 256 + 255 + 1 = 16,777,216)$$

where R, G, and B may each represent a value in the range of [0-255].

For example, for a pixel color having the {R,G,B} measured values {5,100,20} the location (L) on the histogram vector would be:

$$L = 5(256^2) + 100(256) + 20 + 1 = 353,301$$

In this example embodiment, when a same, or similar, color is detected in a selected pixel in an image, a counter associated with location L=353,301, which is initially set to zero, is incremented by one. By way of example, if 155 pixels (other numbers may be used) in a same image have the same or similar (e.g., within a predetermined margin) {R,G,B} values, or the same or similar location (on the histogram) that is derived from the {R,G,B} values, the value of the counter associated with the particular vector location L=353,301 may be set to 155, to indicate 155 occurrences of the same or similar pixel color. In some embodiments, prevalence of pixels' colors in an image may be more important than the exact location of the pixels in the image. In some embodiments, the color histogram may be represented, e.g., as a look-up table or chart, and/or in graphical form, etc.

With respect to the graph of the color histogram, as explained herein, each {R,G,B} combination may be converted to a color value by using a formula, such as, for example, $R*256^2+G*253+B+1$ (which may be scaled, e.g., for viewing purposes, by multiplying the resulting value, e.g., by $10^6$ as shown in FIG. 4). These color values are shown on the graph's horizontal axis. The vertical axis shows the number of times each color value was calculated (e.g., it may show the number of times each color combination was observed), e.g., in each image and/or in the thousands of images. (In this example, the values of the vertical axis were scaled, by taking the natural log of each value). Of course, other formats may also be used for creating the color histogram.

In some embodiments, as explained herein, the color histogram may statistically specify, or indicate, the likelihood of a particular color to appear in a given image, e.g., based on color analysis of a large set, or many sets, of previously taken images. If a particular color is not likely to appear in a given image of a normal or healthy tissue or organ but it does appear in it, this may indicate that the color is likely to represent an anomaly. Furthermore, as explained herein, an analysis of the number of pixels and/or proximity of two or more pixels having a color which is an anomaly (referred to herein as a group or "blob" analysis) may further impact a determination of whether or not a tissue shown in an image actually has an anomaly.

In some embodiments, the color histogram may be created, for example, during a training phase. During the training phase, a variety of images (e.g., videos or image streams including a plurality of images/frames) may be analyzed by anomaly detection software (e.g., anomaly detector 625). The images may contain, for example, "normal", or healthy images (e.g., images known not to have any pathology), "pathology" images (e.g., images known to have a pathology), and/or "unchecked" images (e.g., images which may or may not contain any pathology).

By way of example, for a capsule designed mainly for obtaining images from the colon, an initial color histogram was created by analyzing 56 "training" videos that were marked as 'pathology videos', meaning they contained images with various pathologies (one or more per video). The initial color histogram was created from sampling 'clean'/normal frames in the colon. The number of images sampled per video ranged between 140 and 18,500 frames, and a total of 196,000 frames (from all 56 videos) were processed. The histogram data was then updated during creation of the color histogram with additional normal images in order to enhance it, for example, to decrease false alarms, as will elaborated herein. A total of about 2,000,000 images were sampled.

Similarly, for a capsule designed mainly for obtaining images from the small bowel, an initial color histogram was created by analyzing 51 "training" videos from the 70 "training" videos—21 videos were marked as pathology videos; 30 videos were marked as 'clean'/normal videos. The initial color histogram was created by sampling normal frames in the small bowel. The number of images sampled per video was between 950 and 13,478, and a total of about 200,000 frames were sampled. The histogram data was then updated during creation of the color histogram with additional normal images in order to enhance it, for example, to decrease false alarm, as described herein. A total of about 1,000,000 images were sampled.

In some embodiments, to build a color histogram, a large number of images may be analyzed in terms of color statistics. For example, color 'x' ($\{R_x, G_x, B_x\}$) may appear 100 times in the images/frames, color 'y' ($\{R_y, G_y, B_y\}$) may appear 550 times in the images/frames, etc. In some embodiments, during the training stage, the location of the pixels may play no role; only the number of appearances of individual colors in the image may be taken into consideration. A basic assumption may be that anomaly tissue areas usually manifest colors which are statistically 'rare' in images. An 'anomaly', as understood herein, may refer to anything that can color-wise be distinguished from anything having 'normal' colors, and thus potentially indicate the existence of a pathology.

In accordance with various embodiments, one or more root causes may also be considered. A root cause, as understood herein, is something shown in the image or image data (e.g., something in the GI tract which is captured in an image) which may cause or trigger an 'anomalous' false-alarm for a pixel. For example, in some embodiments, the identification or detection of a pixel as being an 'anomalous pixel' even though the pixel's color is not actually indicative of a pathology is considered to be a false alarm. Common examples of root causes are content, white substances/fluids and/or bubbles passing through the colon or intestine, and/or blood vessels at or near the surface of the walls. Therefore, in some embodiments, a Content Score, White Score, Bubble Score and/or Blood Vessels Score may be calculated to account for the various root causes. More information on these scores can be found in U.S. Pat. Nos. 8,873,816, and 8,861,783, both of which are incorporated herein by reference in their respective entireties.

As in the example above, root causes may be taken into account at the final stage of the creation of the color histogram. During the creation of the color histogram, the ranges of a content score (accounting for content) and/or a white score (accounting for white substances/fluids) of false-alarm anomalous pixels may be checked. Since content scores and white scores may depend only on pixel colors, which may be unique to these phenomena, and, in some embodiments, it may be required or desired not to err on anomalous pixels (e.g., to avoid false alarm(s)), the pixels from which these scores are derived may be singled out and removed from consideration. To that extent, in some embodiments, to finalize the color histogram, histogram values of pixels determined to be root causes may be artificially assigned a higher histogram value (e.g., representing a more common or normal color), as if they were non-anomalous colors. Other root causes (e.g., bubbles for the small bowel and blood vessels for the colon) include pixels with anomalous color, and their colors may be similar to colors that can potentially be pathology (blood, ulcers, red polyps, erosion, etc.). In the final development stage of the color histogram, false alarm frames caused by the root causes would not yet have been factored into the histogram (because the color is similar to pathology color), though the root cause scores (bubble score and blood vessels score) have been checked. For the final algorithm, the root causes are used in determining whether the pixels are anomalous or not by using, for example, specific detectors. For example, anomalous pixels for the small bowel should have relatively low histogram values and they should not be part of bubbles (may be determined by, e.g., using a bubbles detector), and anomalous pixels for the colon should have relatively low histogram values and not be part of blood vessels (may be determined by, e.g., using a blood vessel detector). As such, false-alarm anomalous pixels may not negatively impact the system's ability to detect pathologies.

In some embodiments, prior to analysis and/or as images are analyzed, threshold values may be identified and/or chosen which distinguish normal colors from anomalous colors. Therefore, in some embodiments, the training phase may be based on an iterative process. For example, in some embodiments, as images are analyzed, and more color, pixel, and/or image information is collected by the system, score values and threshold parameters may be updated, e.g., periodically, constantly, etc., to more accurately reflect the distribution, or prevalence, of colors in the analyzed images, and to more accurately delineate the threshold between normal and anomalous colors. In some embodiments, histogram value thresholds may be initially chosen, e.g., anecdotally or based on some ratio, and may be adjusted/corrected over time, as more images are analyzed and more data is collected.

For example, in some embodiments, thresholds may be chosen and/or set by a human, according to the number of false alarm frames estimated or projected or detected. At first, a threshold resulting in a small number of false alarm images/frames may be set. As the histogram data and/or content is updated, the values of the thresholds may be increased, for example, based on the updated data or content, e.g., as the histogram data or content is enhanced with additional information. In some embodiments, each time a small number of false alarm frames are detected, the histogram threshold may be increased, (e.g., the log of the histogram threshold may be increased), for example, by 0.5, 1.0, etc., and/or the size threshold may be increased, e.g., by 10 pixels, 50 pixels, etc. Other incremental adjustments are also possible, including, for example, decreasing thresholds which have been inadvertently or initially set to be too high. In some embodiments, the size thresholds can be decreased as the number of false alarms is decreased. Other incremental adjustments are also possible, including, for example, decreasing thresholds which have been inadvertently or initially set to be too high.

Figure 2:
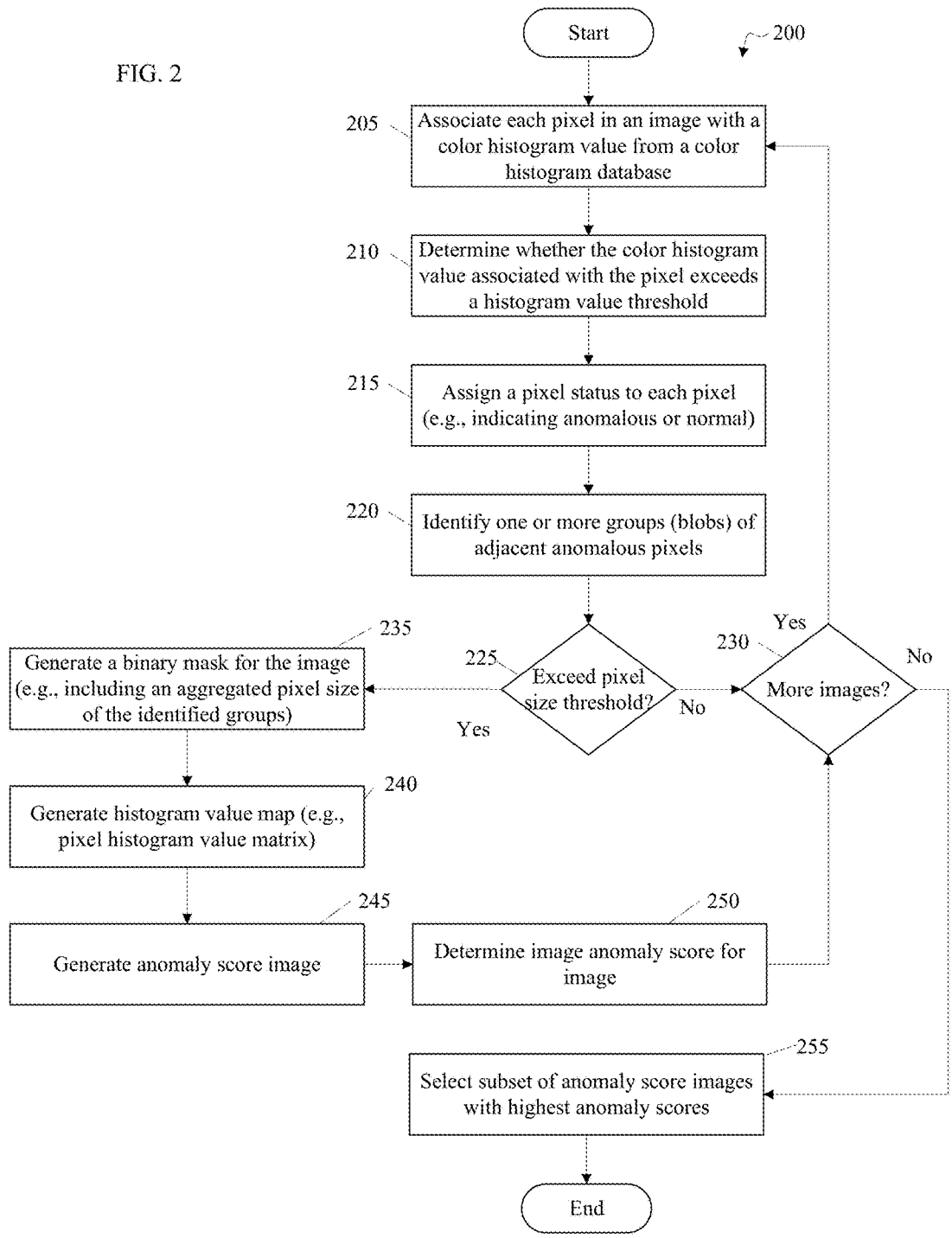
FIG. 2 shows a method for detecting an anomaly in an image captured in vivo by an in-vivo imaging system according to an example embodiment of the invention.

FIG. 2 is a schematic flow diagram illustrating a method 200 of detecting an anomaly in an image captured in vivo by an in-vivo imaging system (such as, for example, the image shown in FIG. 3A) according to at least one embodiment of the invention. In some embodiments, method 200 may be performed on a computer (e.g., computing system 610) having a processor (e.g., controller 605 and/or 651), memory (e.g., memory 624), and one or more code sets or software (e.g., anomaly detector 625) stored in the memory and executing in or executed by the processor.

At step 205, once the histogram database has been created and/or obtained, in some embodiments, the processor may correlate, for each pixel of the image, a histogram value from the histogram database with the pixel. As described herein, in some embodiments, the histogram database is a representation of a distribution (e.g., statistical distribution) or prevalence (e.g., statistical prevalence) of {R,G,B} color values in a set of previously analyzed images. Therefore, in some embodiments, a given histogram value may be a representation of, or an indication to, a distribution, or prevalence, of a particular combination of {R,G,B} color values in a set of previously analyzed images.

In some embodiments, a given histogram value may be correlated with a given pixel, for example, based on the particular combination of {R,G,B} color values which make up the given pixel color in the image. In some embodiments, correlating may include the process of indicating, recording, linking, or otherwise identifying a connection or relationship between a particular color value or combination of color values (e.g., {R,G,B} color values) and a data point or data bucket in a histogram database. For example, a given pixel may be composed of {R,G,B} elements such as {20, 40, 16}. The processor may be configured to locate the entry in the histogram database (e.g., a location in a histogram look-up table) which, in the example, may have a correlating histogram value of 10.5 ($e^{10.5}$=36,315.502, translating to approximately 36,316 instances of the particular combination of {R,G,B} values being identified in the previously analyzed images). Of course, histogram values can range anywhere from zero, a value indicating no instances of a given combination of {R,G,B} elements (the color), up to very large numbers, indicating many occurrences of the combination (the color). It should be noted that, in some embodiments, histogram values may be calculated in, or converted to, log form for ease of use, since the values may become exceedingly large over time.

At step 210, in some embodiments, the processor may determine, for each particular pixel, whether or not the correlated/associated histogram value (e.g., the histogram value associated with the particular pixel) exceeds a histogram value threshold. For example, if the histogram value threshold were set at 12, then, in the example above, the 10.5 histogram value for the pixel with the {R,G,B} of {20, 40, 16} would not exceed the histogram value threshold. In some embodiments, a given correlated histogram value which does not exceed the histogram value threshold indicates an anomalous pixel, and a given correlated histogram value which does exceed the histogram value threshold indicates a normal pixel.

At step 215, in some embodiments, the processor may assign, for each pixel, a pixel status or value which reflects or indicates that the pixel is (e.g., has a status of being) either anomalous or normal (e.g., whether the tissue represented by the pixel is identified, deemed, categorized, or otherwise given a status as anomalous or normal). In some embodiments assigning the pixel status or value to the pixel may be based at least in part on the correlated or associated color histogram value of the pixel. In some embodiments, the pixel status or value of each pixel may be indicated as a binary (base-2) numeral or value, in which, e.g., a "0" indicates a normal pixel, and a "1" indicates an anomalous pixel. Other ways of representing abnormal (anomalous) and normal may be used. In some embodiments, the processor may generate a matrix having the same dimensions (e.g., number rows and columns) as the dimensions of pixels in the image (referred to herein as a "pixel status matrix" or a "binary matrix"). The pixel status matrix may reflect or indicate the pixel status or value of each particular pixel in a corresponding coordinate to that particular pixel in the pixel status matrix, e.g., using zeros and ones or another representation. In some embodiments, the processor may generate a binary representation of the image (e.g., in matrix form, as shown in the pixel status matrix below), in which anomalous pixels are assigned a 1-digit, and normal pixels are assigned a 0-digit.

Example: A Pixel Status Matrix

| 1 | 1 | 1 | 0 | 0 | 0 | 0 | 0 |
|---|---|---|---|---|---|---|---|
| 1 | 1 | 1 | 0 | 1 | 1 | 0 | 0 |
| 1 | 1 | 1 | 0 | 1 | 1 | 0 | 0 |
| 1 | 1 | 1 | 0 | 0 | 0 | 1 | 0 |
| 1 | 1 | 1 | 0 | 0 | 0 | 1 | 0 |
| 1 | 1 | 1 | 0 | 0 | 0 | 1 | 0 |
| 1 | 1 | 1 | 0 | 0 | 1 | 1 | 0 |
| 1 | 1 | 1 | 0 | 0 | 0 | 0 | 0 |

Of course, those of ordinary skill in the art would understand that in various embodiments other numbers, letters, characters, colors, and/or groups thereof etc., may be used to indicate a pixel status or value of each pixel. Furthermore, as discussed herein, in some embodiments, groups or blobs of anomalous pixels (e.g., adjacent anomalous pixels) may be given individual labels, e.g., to further distinguish them from normal pixels and other anomalous pixels.

At step 220, in some embodiments, the processor may identify one or more groups or blobs of adjacent anomalous pixels from among the pixels indicated as anomalous, e.g., in the pixel status matrix. As understood herein, in some embodiments, any two pixels may be considered adjacent if they are directly or immediately next to one another in one or more directions (e.g., up/down, left/right, diagonal, etc.). In some embodiments, two pixels may be considered adjacent if they are sufficiently close (e.g., within 2 pixels, within 3 pixels, etc.) in any direction. Therefore, in some embodiments, a pixel distance threshold may be implemented in which two anomalous pixels within a certain distance of one another may be considered part of the same group. Furthermore, a given anomalous pixel which is equally close to multiple other anomalous pixels may, for example, connect those anomalous pixels (e.g., all the pixels will be considered part of the same blob). Of course, other rules may be implemented, such as, for example, a "gravity" rule, in which single pixels and/or small blobs within a predefined proximity of larger blobs are presumed to "gravitate" toward and be grouped with those larger pixel blobs (and thus be assigned the same representation as the larger blob).

In some embodiments, blobs may be determined by a group of connected pixels: if there is a pixel whose value is '1' (or any particular value), and there is an adjacent pixel (e.g., up/down, left/right, diagonal, etc., relative to the first pixel) with the same value, then the two pixels may be considered part of the same group. In some embodiments, each group of pixels may be assigned a different representation, thus dividing the matrix into distinct groups.

Example: Dividing (Separating) the Pixel Status Matrix into Distinct Groups

| 1 | 1 | 1 | 0 | 0 | 0 | 0 | 0 |
|---|---|---|---|---|---|---|---|
| 1 | 1 | 1 | 0 | 2 | 2 | 0 | 0 |
| 1 | 1 | 1 | 0 | 2 | 2 | 0 | 0 |
| 1 | 1 | 1 | 0 | 0 | 0 | 3 | 0 |
| 1 | 1 | 1 | 0 | 0 | 0 | 3 | 0 |
| 1 | 1 | 1 | 0 | 0 | 0 | 3 | 0 |
| 1 | 1 | 1 | 0 | 0 | 3 | 3 | 0 |
| 1 | 1 | 1 | 0 | 0 | 0 | 0 | 0 |

At step 225, in some embodiments, e.g., in order to limit the number of blobs and/or the number of images to what may be considered a reasonable number ('reasonable' meaning, e.g., a number of blobs and/or images enabling or facilitating fast and/or efficient analysis thereof), an identified group or blob associated with the image may be required to exceed a pixel size or count threshold for that identified group or blob to be considered or used. That is, in some embodiments, individual blobs or groups which do not have a significant enough pixel size to exceed a pixel size or count threshold may be ignored by the system. In some embodiments, at least one of the one or more identified groups or blobs associated with the image may be required to exceed a pixel size or count threshold for the image to be further considered or used. As understood herein, 'pixel size' of a blob or group refers to the number of pixels making, forming, or otherwise included in and/or identified in the blob or group. Additionally, as understood herein, a 'pixel size threshold' is a minimum number of blob pixels and/or group pixels that make the group or blob warrant consideration. For example, a blob/group including a number of pixels equal to or greater than the pixel size threshold may be used to trigger, recommend, request, require, or otherwise indicate that some action can, may or should be taken by embodiments of the system with regard to, for example, that group or blob. In some embodiments, therefore, the system may be configured to identify one or more blobs or groups of adjacent anomalous pixels, in which each blob or group of adjacent anomalous pixels has a pixel size that exceeds a pixel size threshold.

In some embodiments, any blobs which do not exceed the pixel size or count threshold may be considered too small or insignificant to be considered or used. In some embodiments, the pixels which make up such blobs may then be labeled as normal, or the blob may be otherwise masked, ignored, or discarded by the processor, such that the blob will not be identified as a blob of adjacent anomalous pixels. For example, if the pixel size threshold is set at 200 adjacent pixels, a blob including 50 adjacent pixels will not be identified as a blob for the final representation. In some embodiments, if multiple blobs exceed the pixel size threshold, standard computer algorithms (e.g., the "BWLABEL" function available in MATLAB) may be implemented to provide each blob with a different label for identification purposes (as shown in the above example). By using the "BWLABEL" function, the binary image may be divided into connected groups of pixels. Each group may then be checked separately to determine whether or not the specific group is big enough to consider the group as anomaly blob.

In some embodiments, if no blobs or groups of anomalous pixels have been identified in a given image, or if one or more blobs or groups of anomalous pixels have been found but do not meet the threshold criteria as described herein, the given image may be ignored, and, at step 230, additional images in a set of images to which the given image belongs (e.g., additional frames in a video) may be analyzed and/or checked as well. In some embodiments, if no anomaly blobs meeting the threshold criterion described herein have been identified or detected in an image, an image anomaly score value of zero may be assigned to that image. An image anomaly score may describe or reflect the extent (if any) to which anomalous pixel colors are present in an image. Therefore, if no anomaly blobs (blobs or groups of anomalous pixels) are identified in the image, this may be reflected as a zero image anomaly score for the image (e.g., it is likely that there is nothing anomalous about the image, or the image is not regarded as anomalous). If at least one blob meeting the threshold criteria has been identified or detected, some embodiments of the method may continue as described below. If all images in the set have been processed and none of the images indicate or show any anomalies, the series of operations ends. However, as described in detail herein, if at least one image is determined to indicate or show an anomaly (e.g., at least one image includes at least one group or blob that meets the threshold criteria), the series of operations may continue with respect to that image or images.

Figure 5:
FIG. 5 shows an example initial binary mask according to an example embodiment of the invention.

At step 235, if at least one blob which meets the threshold criteria as described herein has been identified in the image (e.g., as described in step 225), in some embodiments, the processor may calculate, produce or generate a binary mask for the image, e.g., using at least the one or more groups of adjacent anomalous pixels, as described herein. As used herein, a 'binary mask' may be an image or other representation which marks, singles out, or otherwise indicates (e.g., visually) all the pixels that are considered or determined to be anomalous pixels. Turning briefly to FIG. 5, an example binary mask is shown according to embodiments of the invention. In some embodiments, a binary mask may include, or result in, an aggregated pixel size of the one or more identified groups or blobs of adjacent anomalous pixels, e.g., an aggregation, accumulation, sum, combination, unification, and/or collection etc., of, or related to, or calculated for, the pixel sizes of each of the one or more identified groups or blobs. In some embodiments, the aggregated pixel size may include a total pixel count of all the anomalous pixels which make up the identified blobs. In some embodiments the aggregated pixel size may only include those identified groups or blobs that exceed the pixel size threshold. In some embodiments, if the color histogram value associated with a pixel is lower than a predefined threshold, its pixel value in the binary mask image may be set at '1' (e.g., represented in the binary mask as white color), and if the histogram value of the pixel is higher than the threshold, its pixel value in the binary mask image may be set at '0' (e.g., represented in the binary mask as black color). In some embodiments, the two binary states in the binary mask image may be represented by other colors, preferably by colors that are color wise distinct from one another.

Figure 6:
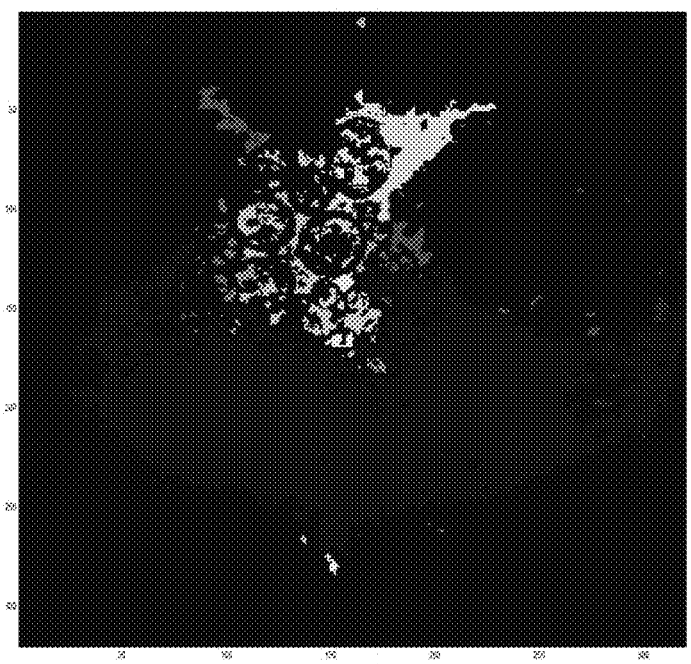
FIG. 6 shows an example partitioned binary mask according to an example embodiment of the invention.

Turning briefly to FIG. 6, in some embodiments, such as when more than one anomaly blob has been identified and each anomaly blob has been assigned a different representation, the binary mask may be partitioned into multiple sections, e.g., represented by different colors. As shown in FIG. 6, each blob of connected white pixels in the binary image (FIG. 5) is given the same color and/or label (black pixels get the value "0"). As such, blobs which are ultimately determined to not be detecting a pathology (e.g., blobs showing one or more root causes, as described herein), or which have a pixel size smaller than a predetermined pixel size threshold, may be excluded from the binary mask.

Figure 7:
FIG. 7 shows an example updated (final) binary mask generated according to an example embodiment of the invention.

Turning briefly to FIG. 7, an updated binary mask is shown according to embodiments of the invention. As compared with the binary mask of FIG. 5, the updated binary mask has fewer 'white' pixels, as blobs of anomalous pixels which were too small (e.g., based on the pixel size threshold) and/or were ultimately determined not to indicate the presence of a pathology, have been removed, discarded, disregarded, and/or otherwise ignored.

Returning to FIG. 2, at step 240, in some embodiments, the processor may generate a histogram value map of the image. As understood herein, a histogram value map associates, links, or maps each pixel in the image to that pixel's corresponding color histogram value in the color histogram database. In some embodiments, the processor may generate the histogram value map in the form of another matrix (referred to herein as a "pixel histogram value matrix"), which, like the pixel status matrix, has the same dimensions (e.g., number rows and columns) as the dimensions of pixels in the image. The pixel histogram value matrix may reflect or indicate the histogram value of each particular pixel in a corresponding coordinate to that particular pixel in the pixel histogram value matrix, e.g., by inserting the correlating color histogram value from the color histogram database in the equivalent coordinate in the matrix.

Figure 3A:
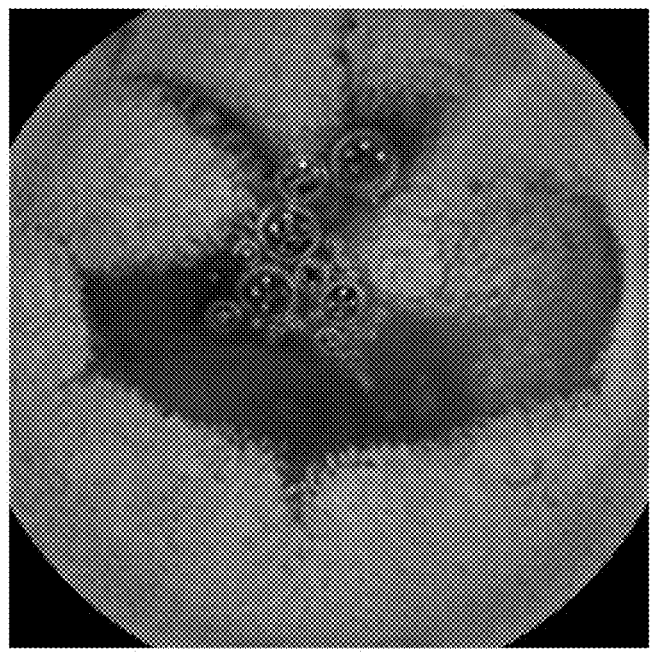
FIGS. 3A and 3B depict an example {R,G,B} image and a corresponding processed anomaly score image respectively, according to an example embodiment of the invention.
Figure 3B:
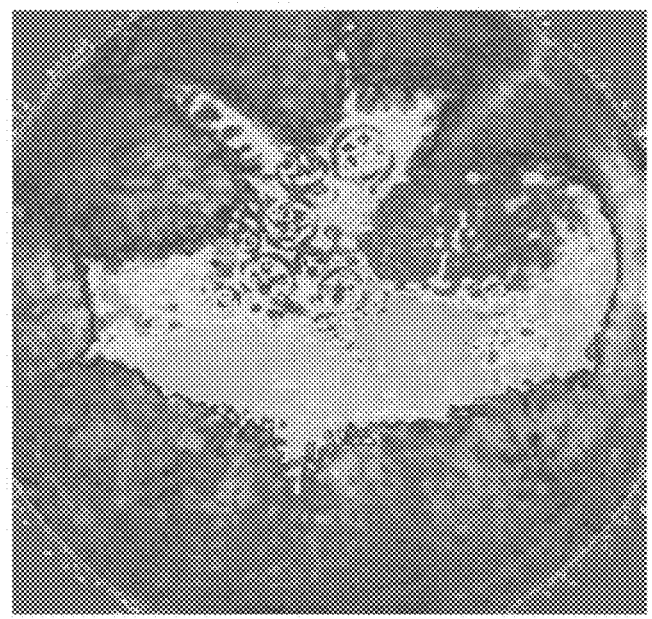

At step 245, in some embodiments, the processor may further use the pixel histogram value matrix to generate a corresponding processed image, referred to as an anomaly score image, e.g., as shown in FIG. 3B. In some embodiments, the anomaly score image may be a topographical image, as described herein. The topographical image provides a topographical (e.g., relating to or representing the physical distribution of parts or features on the surface of or within an organ or organism), color-mapped representation of the potential levels of anomaly which may be detected by further embodiments of the invention. Color mapping, as understood herein, is a function that maps (transforms, replaces, etc.) the colors of one (source) image, palate, profile, etc., to the colors of another (target) image. A color mapping may be referred to as the algorithm that results in the mapping function or the algorithm that transforms the image colors.

FIG. 3B shows, for each pixel in the image of FIG. 3A, how "regular" or common the color of each pixel is (e.g., not an anomalous pixel). The anomaly score image (e.g., topographical color-mapped image), which, in this embodiment, was mapped to a standard ("Jet") color map to generate the image, functions similarly to a thermal image, emphasizing anomalous pixels/blobs. In this example embodiment the more a pixel's color is red, such as, e.g., pixel 310, the more the pixel's {R,G,B} value is common, meaning that its histogram value is higher, and the more the pixel's color is blue, such as, e.g., pixel 320, the less common the pixel's RGB value is (and the more it is 'anomalous'), meaning that its histogram value is lower. Of course, other color maps may also be used, and/or other types of anomaly score images may be generated, such as, e.g., an anomaly area image (described herein).

Returning to FIG. 2, at step 250, in some embodiments, the processor may determine an image anomaly score for the image. In some embodiments, the image anomaly score is determined based on a pixel size of the final binary mask of the image (e.g., the total pixel count of the final binary mask) and a mean histogram value (e.g., the mean of the set of histogram values) of one or more pixels in the binary mask. In some embodiments, the image anomaly score may be calculated using a formula such as, for example:

Small Bowel Image Anomaly Score=
  $\log_{10}[|\text{Mask Size}|$
  $*(\text{histogram value threshold}-\text{mean}(\text{mask histogram values}))]$

OR

Colon Image Anomaly Score=
  $\log_{10}[\sqrt{|\text{MaskSize}|}$
  $*(\text{histogram value threshold}-\text{mean}(\text{mask histogram values})]$ Using the above formulas, for example, which factor in both the mask size and the histogram value parameters (e.g., from the histogram value map and/or from the color histogram), the output value of the formulas will typically be in the range 0 to 255. Of course, other formulae may also be used to calculate the anomaly score. As such, presuming the other variables are held constant, an image with a larger binary mask will have a higher image anomaly score. Likewise, presuming the other variables are held constant, an image with a smaller mean mask histogram value may also result in a higher image anomaly score. Conversely, an image with a smaller binary mask or a larger mean mask histogram value, presuming other variables are held constant, may have a lower image anomaly score comparatively. Using the above equation, for example, the processor may determine an image anomaly score based on the correlated histogram value of each pixel in the image, and the binary mask, e.g., for each image identified as having at least one anomalous blob with the requisite pixel size.

Figure 8A:
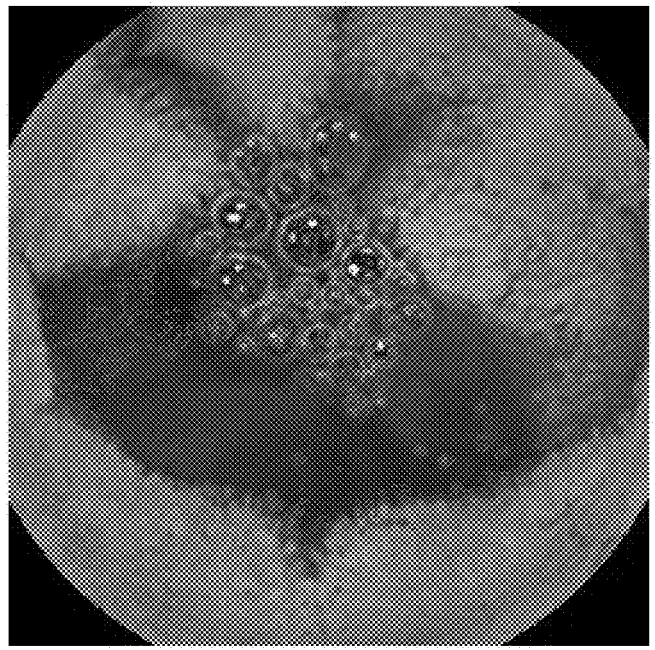
FIG. 8A shows the boundaries of the binary mask image of FIG. 5 overlaid on the image of FIG. 3A according to example embodiments of the invention.
Figure 8B:
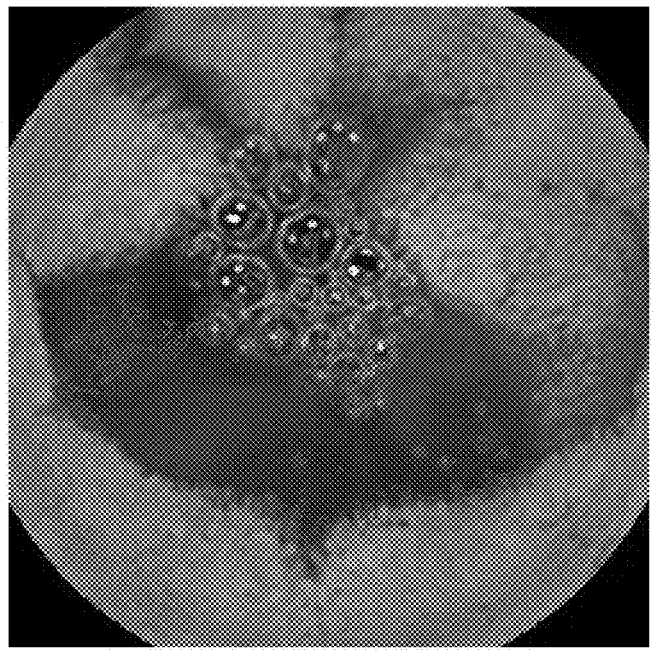
FIG. 8B shows the boundaries of the updated binary mask image of FIG. 7 overlaid on the image of FIG. 3A according to example embodiments of the invention.

Furthermore, in some embodiments, using the correlating histogram values, the processor may be configured to generate anomaly area images (as described herein) for each image containing an identified anomaly blob. By way of example, turning briefly to FIG. 8A, the image of FIG. 3A is shown with an area mask (outline) 810a generated by outlining the area where anomaly blobs were indicated by the initial binary mask of FIG. 5 and overlaying the boundaries on the image. By way of another example, turning briefly to FIG. 8B, the image of FIG. 3A is shown with an area mask (outline) 810b generated by outlining the area where anomaly blobs 820b were indicated by the update (final) binary mask of FIG. 7 and overlaying the boundaries on the image. Note, in one embodiment normal pixels, e.g. pixels 830b, are not bounded. A comparison of FIGS. 8A and 8B shows that bubbles, white areas, and content have been removed from inclusion in the final areas indicated as having anomaly blobs.

In some embodiments, if all desired images have been evaluated (e.g., all images in the set of images have been evaluated for the presence of anomalous pixels/blobs as described herein, shown as the "No" condition at step 230), then, at step 255, in some embodiments, the processor may select, for a set of generated anomaly score images, a subset of anomaly score images with (e.g., that have) corresponding images having the highest, or relatively high image anomaly scores (e.g., based on a predetermined percentile scale, such as top 1%, top 5%, etc. or a predetermined number), and, for example, display the subset of anomaly score images to a user or add them to a set of images displayed to a user, e.g., to enhance the set of images. For images of the colon, in some embodiments, no more than, for example, 100 anomaly score images may be selected, and for images of the small bowel, in some embodiments, no more than, for example, 20 anomaly score images may be selected. If there are more anomaly score images (e.g., with score values greater than 0) than the respective 'budget' (e.g., 100 or 20), in some embodiments, images with the highest score (e.g., based on some predetermined threshold) may be selected or taken.

In some embodiments, if an anomaly was detected in an image, in addition to the determination of an image anomaly score and generation of an anomaly score image, information related to a result or indication to be provided to a user may be recorded or updated. For example, a frame number or a time stamp may be recorded, etc., e.g., to be provided at a later time. Alternatively, an indication to a user may be provided substantially immediately upon detecting an anomaly. Updating results or reporting, upon termination of the method, may include any relevant task. For example, the processor may update and maintain a list of images/frames in which anomaly was detected, the list may be updated, e.g., to indicate a frame number, a time parameter (e.g., the elapsed time from the capturing a first frame in a video stream to the capturing of a specific frame) or any other parameter or reference.

In some embodiments, a result or indication may be provided in the form of, e.g., a list or display of one or more frames in which at least one anomaly blob was identified. A list or display of frames may be provided to a physician, e.g., on a monitor, thus eliminating the need to spend time watching an entire video stream (that may be very long) in search of anomalies. Rather, the physician may be provided with selected frames (according to a list) and only examine selected frames. Updating anomaly results may include presenting or updating a presentation of results on a display screen, e.g., marking a detected anomaly.

Embodiments of the invention may include an article such as a computer or processor non-transitory readable medium, or a computer or processor non-transitory storage medium, such as for example a memory, a disk drive, or a USB flash memory, encoding, including or storing instructions, e.g., computer-executable instructions, which when executed by a processor or controller, carry out methods disclosed herein. For example, a system may include a non-transitory storage medium such as memory 620, computer-executable instructions such as anomaly detector 625 and a controller such as controller 605. Some embodiments may be provided in a computer program product that may include a non-transitory machine-readable medium, having stored thereon instructions, which may be used to program a computer, or other programmable devices, to perform methods as disclosed above.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

The invention claimed is:

1. A method for detecting an anomaly in an image from a set of images captured in vivo by an in-vivo imaging system, performed on a computer having a processor, a memory, and one or more code sets stored in the memory and executing in the processor, the method comprising:

for each pixel of the image, associating the pixel, by the processor, with a color histogram value from a color histogram database, wherein the color histogram database includes color histogram values, each indicative of a likelihood of a particular color to appear in an image captured in vivo based on a color analysis of one or more sets of in vivo images previously taken by an in vivo imaging system;

assigning, by the processor, a pixel status for each pixel of the image indicating whether the pixel is anomalous or normal, wherein the pixel status is determined by comparing the color histogram value to a histogram value threshold and wherein the histogram value threshold is determined based on said color histogram database;

identifying in the image, by the processor, one or more groups of adjacent anomalous pixels; and providing a user, by the processor, with a result based on one or more images of said set of images captured in-vivo in which at least one group of adjacent anomalous pixels was identified, thereby indicating to the user in vivo areas suspected as having an anomaly.

2. The method as in claim 1, wherein the color histogram database is a representation of a prevalence of {R,G,B} color values in the one or more sets of the previously taken in vivo images.

3. The method as in claim 1, wherein a given color histogram value is a representation of a prevalence of a particular combination of {R,G,B} color values in the one or more sets of previously taken in vivo images; and wherein the given color histogram value is associated with the given pixel based on the particular combination of {R,G,B} color values which make up the given pixel color in the in vivo image.

4. The method as in claim 1, wherein the pixel status of each pixel is indicated as a binary value.

5. The method as in claim 1, wherein each of the one or more identified groups of adjacent anomalous pixels is of a pixel size that exceeds a pixel size threshold.

6. The method as in claim 1, further comprising:
generating, by the processor, using at least the one or more groups of adjacent anomalous pixels, a binary mask for the image; and
determining, by the processor, an image anomaly score for the image based at least in part on the binary mask,
wherein said result referring to one or more images is based on said image anomaly score of said one or more images.

7. The method as in claim 6, wherein the image anomaly score is determined based on a pixel size of the binary mask of the image and a mean histogram value of one or more pixels in the binary mask.

8. The method as in claim 6, further comprising generating an anomaly score image based on the correlated histogram value of each pixel in the image, and the binary mask.

9. The method as in claim 8, further comprising:
for a set of generated anomaly score images, selecting, by the processor, a subset of the anomaly score images with the highest image anomaly scores;
wherein the providing of the result comprises displaying the subset of anomaly score images to the user or adding them to a set of images displayed to the user.

10. The method as in claim 1, wherein the set of images is captured while the in-vivo imaging system moves through the gastrointestinal system.

11. The method as in claim 1, wherein the color histogram database represents prevalence of colors that appear in the previously taken one or more sets of images, and wherein the previously taken one or more sets of images were taken inside the gastrointestinal system.

12. The method as in claim 1, further comprising generating the color histogram database based on said one or more sets of previously taken in vivo images.

13. The method of claim 12, further comprising updating the color histogram database with additional images.

14. The method of claim 12, wherein the generating of the color histogram database further comprises assigning values representing non-anomalous colors to false-alarm anomalous colors which are unique to certain phenomena.

15. The method as in claim 1, further comprising setting the histogram value threshold to distinguish normal colors from anomalous colors.

16. The method of claim 1, wherein the images of the one or more sets of previously taken in vivo images are normal images of healthy tissue.

17. A system for detecting an anomaly in an image from a set of images captured in vivo by an in-vivo imaging system, comprising:
a processor;
a memory; and
one or more code sets stored in the memory and executing in the processor, which, when executed, configure the processor to:

for each pixel of the image, associate the pixel with a color histogram value from a color histogram database, wherein the color histogram database includes color histogram values, each indicative of a likelihood of a particular color to appear in an image captured in vivo based on a color analysis of one or more sets of in vivo images previously taken by an in vivo imaging system;
assign a pixel status for each pixel of the image indicating whether the pixel is anomalous or normal, wherein the pixel status is determined by comparing the color histogram value to a histogram value threshold and wherein the histogram value threshold is determined based on said color histogram database;
identify in the image one or more groups of adjacent anomalous pixels; and
provide a user with a result based on one or more images of said set of images captured in-vivo in which at least one group of adjacent anomalous pixels was identified, thereby indicating to the user in vivo areas suspected as having an anomaly.

18. The system as in claim 17, wherein the color histogram database is a representation of a prevalence of {R,G,B} color values in the one or more sets of the previously taken in vivo images.

19. The system as in claim 17, wherein a given color histogram value is a representation of a prevalence of a particular combination of {R,G,B} color values in the one or more sets of previously taken in vivo images; and
wherein a given color histogram value is associated with a given pixel based on the particular combination of {R,G,B} color values which make up the given pixel color in the in vivo image.

20. The system as in claim 17, wherein the pixel status of each pixel is indicated by a binary value.

21. The system of claim 17, wherein the images of the one or more sets of previously taken in vivo images are normal images of healthy tissue.

22. The system of claim 17, wherein the code, when executed, configures the processor to:
generate using at least the one or more groups of adjacent anomalous pixels, a binary mask for the image; and
determine an image anomaly score for the image based at least in part on the binary mask.

23. The system as in claim 22, wherein the one or more code sets further configure the processor to determine the image anomaly score based on a pixel size of the binary mask of the image and a mean histogram value of one or more pixels in the binary mask.

24. The system as in claim 22, wherein the one or more code sets further configure the processor to: generate an anomaly score image based on the correlated histogram value of each pixel in the image, and the binary mask.

25. The system as in claim 24, wherein the one or more code sets further configure the processor to:
for a set of generated anomaly score images, select a subset of the anomaly score images with the highest image anomaly scores
wherein the providing of the result comprises displaying the subset of anomaly score images to the user or adding them to a set of images displayed to the user.

* * * * *